United States Patent

Nason et al.

[11] Patent Number: 5,807,699
[45] Date of Patent: Sep. 15, 1998

[54] APPARATUS AND METHOD FOR MONITORING CONDITION OF A BIOMASS

[75] Inventors: Robert Brian Nason, Darenth; John Melvin Clark Reid, Crowborough; John Timothy Fisher, Wickford, all of England

[73] Assignee: Thames Water Utilities Limited, Reading, England

[21] Appl. No.: 307,813
[22] PCT Filed: Mar. 25, 1993
[86] PCT No.: PCT/GB93/00618
 § 371 Date: Feb. 13, 1995
 § 102(e) Date: Feb. 13, 1995
[87] PCT Pub. No.: WO93/20436
 PCT Pub. Date: Oct. 14, 1993

[30] Foreign Application Priority Data

Mar. 27, 1992 [GB] United Kingdom .................. 9206796

[51] Int. Cl.⁶ ................ C12Q 1/18; C12M 1/34
[52] U.S. Cl. .......................... 435/32; 435/29; 435/286.5; 435/287.1; 435/287.5; 436/62; 422/79; 210/614
[58] Field of Search .................. 435/4, 3, 29, 30, 435/31, 286.5, 286.6, 287.1, 287.5; 436/62; 422/79; 210/614; 73/1.02, 1.03

[56] References Cited

U.S. PATENT DOCUMENTS

| | | | |
|---|---|---|---|
| 3,684,702 | 8/1972 | Hartmann | 435/287.5 |
| 3,740,320 | 6/1973 | Arthur. | |
| 4,073,892 | 2/1978 | Ciaccio et al. | 195/103.5 R |
| 4,260,490 | 4/1981 | Moss et al. | 210/620 |
| 4,329,232 | 5/1982 | McKenna | 210/614 |
| 4,783,750 | 11/1988 | Smith | 210/614 |
| 5,106,511 | 4/1992 | Kodukula | 210/614 |

FOREIGN PATENT DOCUMENTS

| | | | |
|---|---|---|---|
| 2308933 | 11/1976 | France. | |
| 2952343 | 6/1981 | Germany | 436/62 |
| 257124 | 6/1988 | Germany | 436/62 |
| 53-116892 | 10/1978 | Japan | 436/62 |

OTHER PUBLICATIONS

Patent Abstracts of Japan, vol. 8, No. 169, Aug. 4, 1984.
Patent Abstracts of Japan, vol. 6, No. 183, Sep. 18, 1982.

*Primary Examiner*—William H. Beisner
*Attorney, Agent, or Firm*—Alix, Yale & Ristas, LLP

[57] ABSTRACT

The invention relates to apparatus (1) for monitoring condition of a biomass, particularly that naturally occurring in activated sewage sludge, comprising a vessel (2) for holding a liquid in the form of the activated sewage sludge containing a biomass (3), a device in the form of an aeration ring (4) for continuously aerating the sludge (3) in use, a hopper (5) and valve V2 arrangement to dose the biomass (3) in the vessel (2) with an additive in the form of an additional dose or charge of a feed solution, and a dissolved oxygen probe (6) to measure the dissolved oxygen content of the sewage in the vessel (2) whereby to monitor the condition of the biomass. Poisoning of the biomass is detected using the probe and associated electronic equipment (FIG. 3), such poisoning being shown by a sudden reduction in the measurement of the current of oxygen used per dose of sewage feed solution.

17 Claims, 3 Drawing Sheets

APPARATUS AND METHOD FOR MONITORING CONDITION OF A BIOMASS

BACKGROUND OF THE INVENTION

The invention relates to apparatus and method for monitoring condition of a biomass, particularly a nitrifying biomass naturally occurring in sewage.

Toxicants or toxic materials present in activated sewage sludge need to be determined so that the source of those toxins can be identified and controlled. Indeed, the activated sludge process is prone to poisoning by a number of agents, the first indication of which may often be the sudden and complete loss of nitrification, in a sewage treatment works, with all of its associated hazards such as fish kills and the placing of an unacceptably high ammonia load on any watercourse receiving the works' effluent. Thus illegal discharge of for example cyanides/plating compounds in trade effluent can poison nitrifying organisms in the sewage sludge, so that nitrification is ceased and an unacceptably high level of $NH_3$ ions in the effluent results which can for example kill fish even if cyanide present does not.

SUMMARY OF THE INVENTION

It is accordingly an object of the invention to seek to mitigate this disadvantage.

According to a first aspect of the invention, there is provided apparatus for monitoring condition of a biomass, comprising a vessel for holding a liquid containing a biomass, a device for continuously aerating the liquid in use, means to dose this liquid periodically with feed solution, and means to measure dissolved oxygen content of the liquid whereby to monitor the condition of the biomass, characterised by a pump for continuously feeding the dosing means with a feed solution.

Using the invention, it is possible to monitor continuously the condition of the biomass by assessing the amount of oxygen being consumed, and thereby to determine whether the biomass, and hence liquid in which it is maintained, has been poisoned by toxic addition.

There may be means to remove liquid suitably effluent, and means to maintain a substantially constant temperature.

The aeration device may comprise an aeration ring connected with an air pump via a solenoid. This provides for a relatively simple way of ensuring oxygen addition over substantially the whole surface area of the vessel, i.e. aeration and mixing.

The dosing means may comprise a receptacle, and a valve which is periodically actuated to discharge a dose of feed solution into the vessel. This provides for a consistent operation of the apparatus.

The pump may comprise a peristaltic pump which may feed the feed solution continuously to the receptacle. This provides for a 24 hour monitoring of the feed solution(s).

The means to measure dissolved oxygen content may comprise a probe, and may include means to calibrate the probe, and to check, preferably automatically, the probe. This provides for repeatability of operation of the apparatus.

The calibration means may comprise means to raise the probe from the liquid, means to add a calibrating solution to the probe, and means to expose the probe to substantially 100% humid air in a headspace of the vessel. This again provides for repeatability and therefore consistency of operation, as well as for providing a check of the probe against 100% humidity and a check of the biomass for nitrification.

The means to raise the probe may comprise a rack and pinion mechanism operated by a reversible motor. This provides for a positive action. The apparatus may include a means within the vessel whereby to clarify liquid prior to removal from the vessel.

The clarifying means may comprise an inverted cylinder within the vessel in which the liquid is clarified. This provides a relatively simple way of clarifying the liquid, but in such a way that the liquid can be mixed by reversing flow of air to the vessel.

The clarifying means may also be automatically cleaned to remove any accumulated solids.

The apparatus may include electronic data processing means whereby operation of the apparatus may be controlled. This provides for simplified control of the apparatus.

According to a second aspect of the invention, there is provided a method of monitoring condition of a biomass, comprising the steps of providing a liquid containing a biomass, continuously aerating the liquid-containing biomass, periodically dosing the liquid with feed solution, and measuring the dissolved oxygen content of the biomass whereby to monitor the condition of biomass, the dosing means being continuously fed with a feed solution.

The step of measuring the dissolved oxygen content may be an electronically controlled measuring step whereby to establish the efficacy of oxygen consumed by the biomass. Stated in another way, dissolved oxygen (DO) is measured to determine the oxygen amount used by the biomass for each addition of feed solution.

The provision of the liquid may comprise providing sewage from a sewage treatment plant.

The method may include the steps of receiving data relating to sewage flow and combining that flow data with the biomass condition whereby to calculate loadings in a sewage treatment plant. This provides for automated control of a sewage plant. Preferably the data is a flow signal in analogue form at 4–20 mA.

The method may include the step of monitoring the condition of the biomass at an inlet to the plant and at an exit from a primary tank, whereby to provide data relating to oxygen demand of the plant. Stated in another way, the apparatus, or monitor may be sited at an inlet or an outlet of a sewage treatment works in order to feed with crude or settled sewage and therefore provides a sewage dosing agent or feed solution, and controls aeration.

The method may include the step of determining toxicity of the feed solution when a change in the condition of the biomass is detected.

BRIEF DESCRIPTION OF THE DRAWINGS

Apparatus embodying the invention is hereinafter described, by way of example, with reference to the accompanying drawings.

DESCRIPTION OF THE PREFERRED EMBODIMENT

Figure 1:
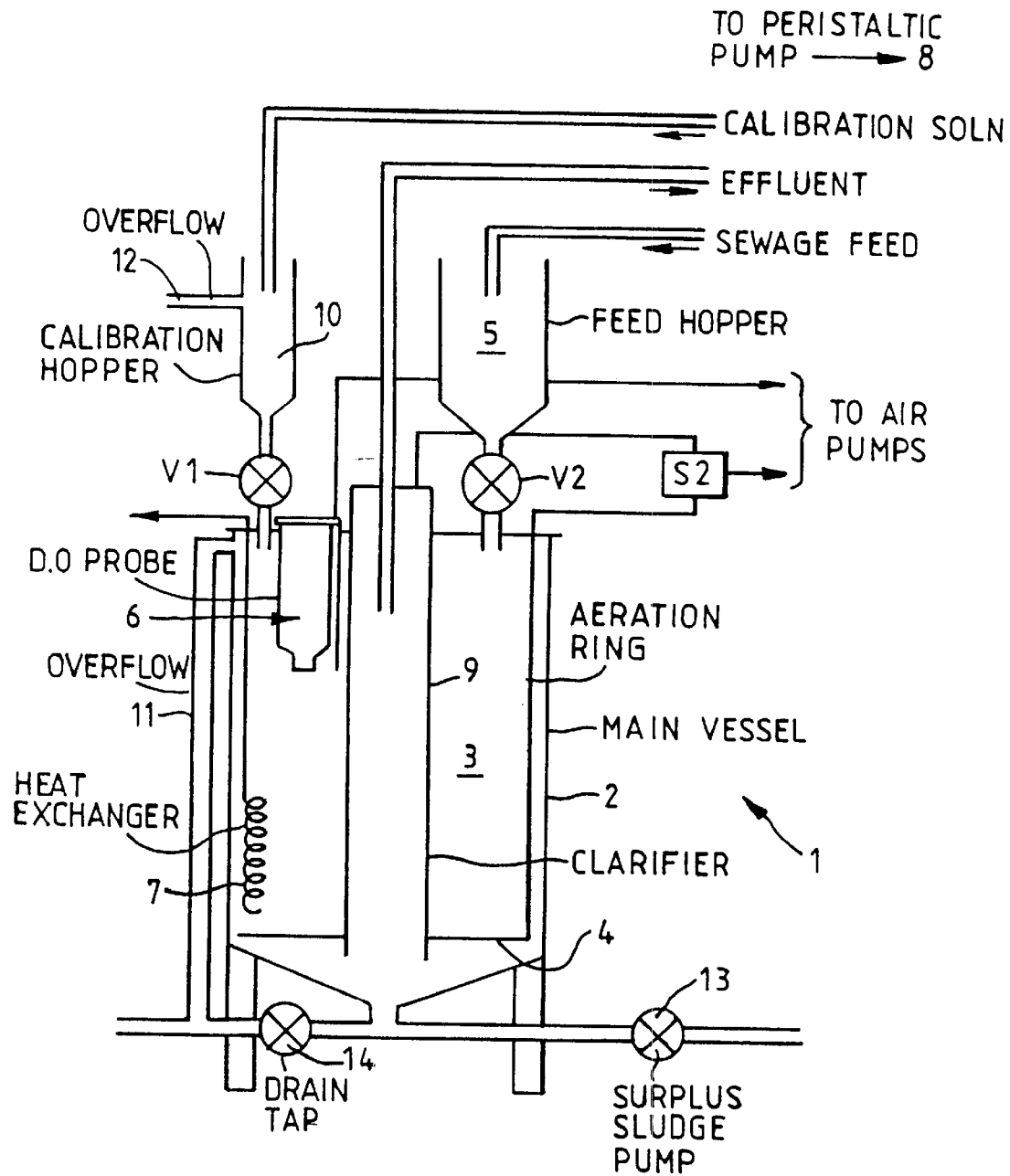
FIG. 1 is a schematic side elevational view of apparatus according to the invention for monitoring the condition of a biomass derived from activated sludge in a sewage treatment plant.
Figure 2A:
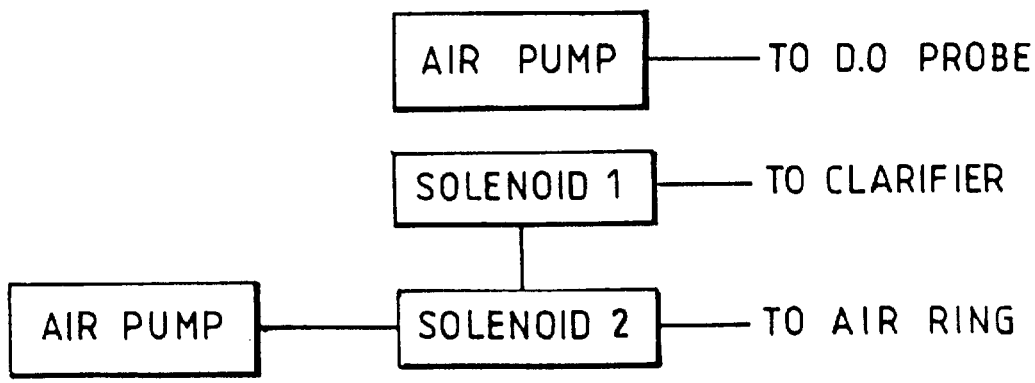
FIG. 2 shows schematically a flow diagram for air flow in air lines in the apparatus of FIG. 1.
Figure 2B:
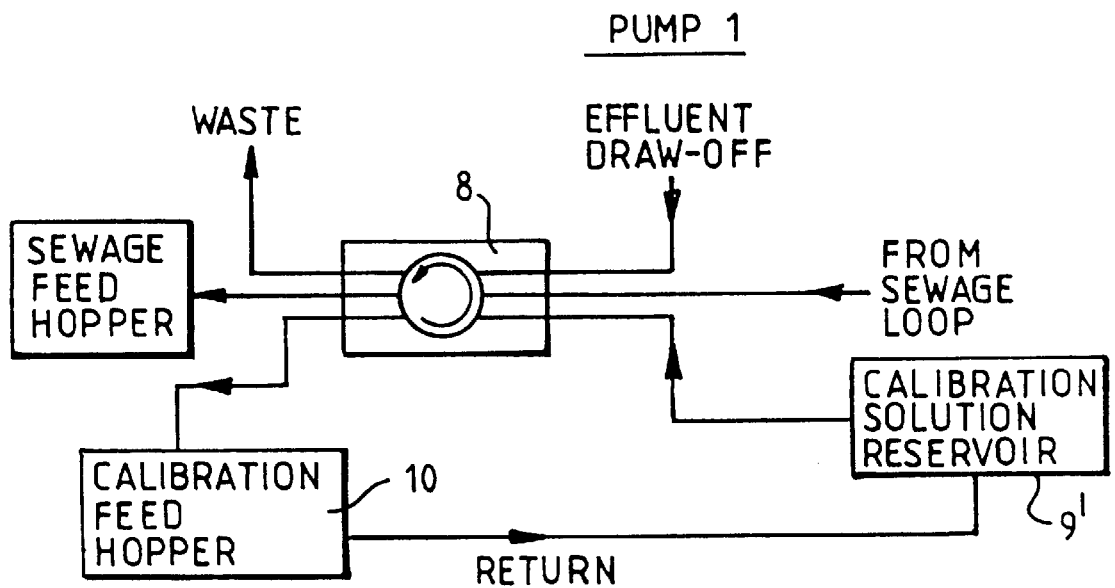
Figure 2C:
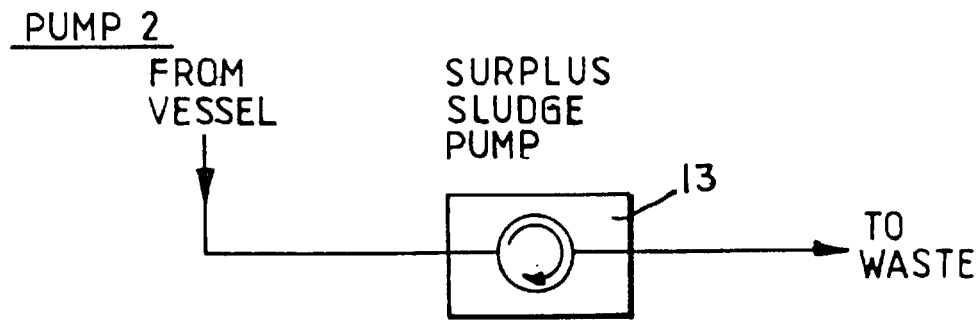
Figure 3:
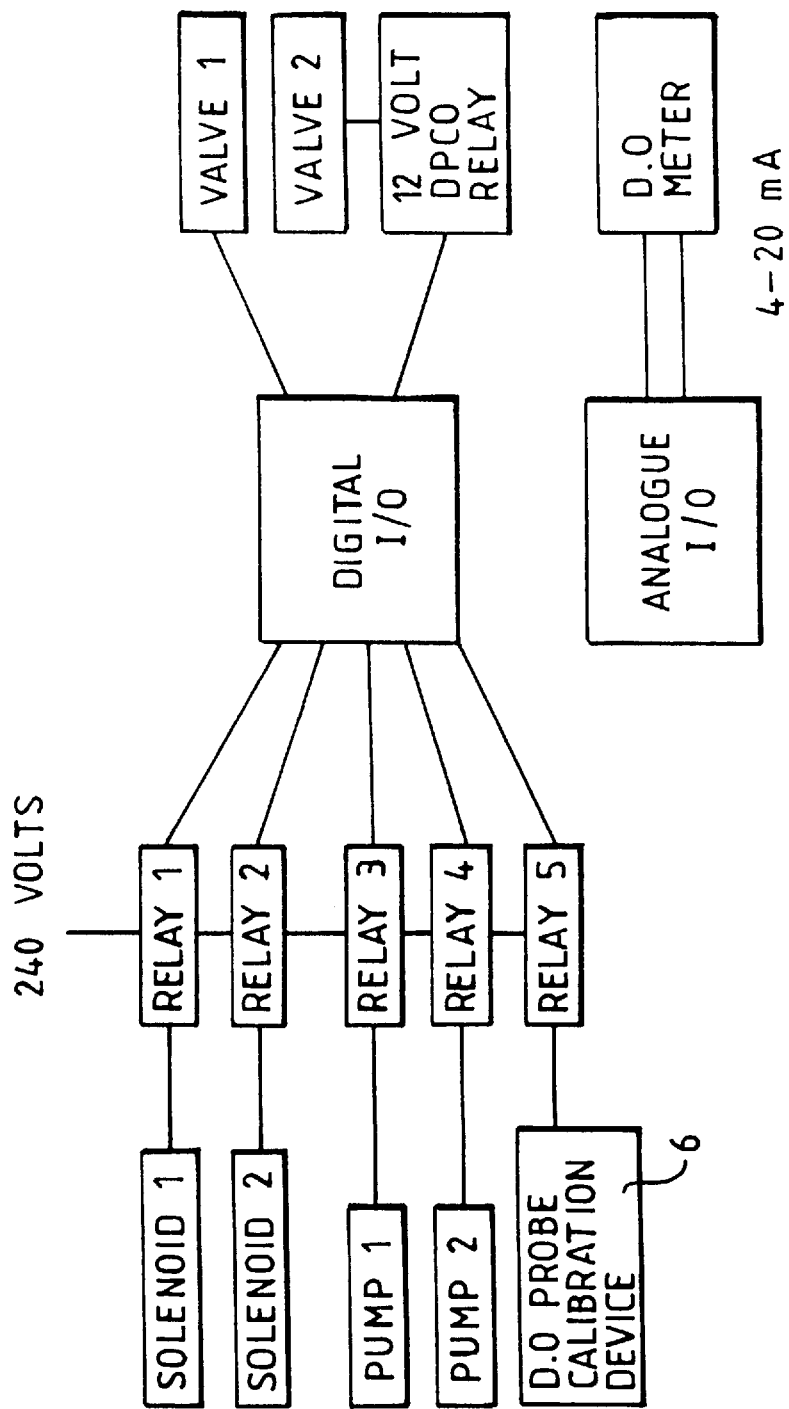
FIG. 3 shows schematically a wiring diagram of the apparatus of FIG. 1.

Referring to the drawings, particularly FIG. 1, there is shown apparatus 1 for monitoring condition of a biomass, particularly that naturally occurring in activated sewage sludge, comprising a vessel 2 for holding a liquid in the form of the activated sewage sludge containing a biomass 3, a device in the form of an aeration ring 4 for continuously aerating the sludge 3 in use, means in the form of a hopper 5 and valve V2 arrangement to dose the biomass 3 in the vessel 2 with an additive in the form of an additional dose or charge of a feed solution, and means in the form of a dissolved oxygen probe 6 to measure the dissolved oxygen content of the sewage in the vessel 2 whereby to monitor the condition of the biomass. Poisoning of the biomass is detected using the probe and associated electronic equipment (FIG. 3), such poisoning being shown by a sudden reduction in the measurement of the current of oxygen used per dose of sewage feed solution.

The biomass has been poisoned as it is not active in removing the oxygen from the sludge 3, toxicity being detected at a much lower level than heretofore owing to inhibition of nitrification.

Thus the apparatus 1 comprises a monitor which detects toxic substances harmful to a sewage treatment process and provides an electronic signal proportional to the strength of the sewage. The information or data can then be used to calculate loadings on a sewage treatment plant or works when flow data of sewage into or through the works is known.

The apparatus 1 is suitable to be mounted in a mobile unit such as a towable van (not shown) which can be transported to a desired site or works and connected with the sewage flow by any suitable means such as piping. It will be understood too that the apparatus can equally well be a permanent installation or a piece of laboratory equipment.

The vessel 2 in the embodiment is a cylindrical P.V.C. vessel which has a volume sufficient to hold about 10 liters of biomass in the form of activated sludge 3. The aeration ring provides air from a compressor at a constant rate for aerating the biomass. There is within the vessel 2 a heat exchanger 7 which maintains the biomass at a constant temperature by a heater/cooler unit. The sewage or feed solution is fed to the vessel 2 by a peristaltic pump 8 which feeds the biomass to the hopper 5 which is periodically emptied into the vessel through the valve V2 which is operated by a solenoid.

There is suspended within the vessel a clarifier in the form of an inverted cylinder 9 in which the suspended biomass enters a quiescent zone and thereby enables clear effluent to be withdrawn using the peristaltic pump 8. The clarifier 9 is purged by a separate air supply to the aeration ring 4, which automatically cleans the clarifier 9. The contents of the vessel 2 are maintained fully mixed by the aeration system and this thus provides for a uniform reading.

The dissolved oxygen probe 6 is calibrated regularly, usually once a day, by exposing it to 100% humid air in a headspace of the vessel. Also the probe 6 is raised from the biomass for calibration and cleaning by being mounted on a rack and pinion mechanism operated automatically by a reversible motor, the probe being cleaned by a feed of air thereto when it is removed from the sewage by air from the air feed from an air pump feeding air through a pipeline to a jet adjacent the (raised) probe.

There is a constant level device 12 in a calibration hopper 10 to maintain constant volume, there being an overflow 11 from the vessel 2, as an additional safety check. The base of the vessel 2 is conical to collect settled solids and from which surplus biomass can be withdrawn via a pump 13, there also being a suitable drain tap 14.

In use the various feeds and valves V1, V2 are operated electronically by a computer (FIG. 3) to monitor the condition of biomass in the vessel 2 which comprises aerating the biomass continuously via the aeration ring 4, and measuring the dissolved oxygen content thereof periodically, say every twenty seconds. These readings are logged; a feed solution is fed continuously to the hopper 5, which is emptied every 30 minutes through the valve V2. As each of these feeds is added, the dissolved oxygen level drops until it reaches a minimum and then rises until it levels off ready for the next feed of sewage. The effect of this is to produce an inverse 'saw tooth' or 'inverse peak' plot of the dissolved oxygen readings on say an oscilloscope. The computer integrates these inverse peaks and stores them, suitably on disc, each peak area being a measure of the amount of oxygen consumed by the biomass per feed.

Likewise, the amount of oxygen is proportional to the strength of the sewage. The computer then utilises the peak area to calculate the strength of the sewage using calibration coefficients which can in any event be obtained from automatic calculations which are made daily at a sewage treatment plant. When there is no toxic load, the inverse peaks are produced and noted. However if a toxic charge is delivered to the sewage and hence enters the vessel when dosing takes place, the biomass is poisoned and oxygen consumption is reduced. This leads to a reduction in the area of the inverted peak, and in extreme cases can lead to a flattening out of the peaks. The computer compares consecutive peak areas, and if there is a reduction of a particular desired amount, which is 40% in the embodiment (the reduction "trigger" is adjustable by an operator according to prevailing conditions) then the computer identifies this as a toxic load. An alarm, which may be audible, visual, or both, or a digital (electronic) contact closure is given, and a sampler is activated to take samples of the feed solution so that the kind, and hence source, of the toxic contaminant can be identified.

As has been referred to above, the probe 6 is cleaned and calibrated automatically once a day.

The cleaning and calibration cycle works in the following manner:

At a pre-determined time (early hours of the morning) the feed pump 8 is switched off after the last feed. An air pump provides air to the clarifier and DO probe, via a solenoid S2, and the clarifier 9 purged for 1 minute. A solenoid is then switched to divert air onto the membrane of the dissolved oxygen probe for 5 minutes. After this the probe 6 is removed as by lifting from the liquid and once a stable dissolved oxygen reading is obtained the computer then proceeds to recalibrate the dissolved oxygen probe 6. It does this by reading the temperature of the vessel headspace into which the probe is lifted, via a thermocouple and using a 'look up' table to obtain the correct dissolved oxygen The probe is then returned to the liquid 3. A surplus feed solution pump 15 is turned on for a pre-determined amount of time during cleaning of the clarifier and cleaning of the probe before the probe is removed from the biomass.

The computer then waits for feed valve V1 to open again and when it closes, the feed pump is switched back on and valve V2 is opened emptying the calibration solution into the vessel. Once this peak area has been integrated, the value of this peak area is confirmed to be within defined limits to confirm that the biomass is nitrifying satisfactorily. If it is not, a warning message is displayed to the operator to check operating conditions. The apparatus then returns to normal operation.

Using an apparatus and method according to the invention can result in strength determination (a measure of the amount of polluting material present) and toxicity detection of substances inhibitory to the biomass such as cyanides, organic chemicals and the like.

We claim:

1. Apparatus for monitoring condition of a biomass, comprising a vessel for holding a liquid containing the biomass, a device for continuously aerating the liquid during monitoring of the biomass, means to dose the liquid periodically with feed solution, a pump, control means which maintains the pump in continuous operation for continuously feeding the dosing means with the feed solution during monitoring of the biomass, and means to measure dissolved oxygen content of the liquid whereby to monitor the condition of the biomass.

2. Apparatus according to claim 1, the aeration device comprising an aeration ring connected with an air pump via a solenoid.

3. Apparatus according to claim 1, wherein the dosing means comprises a receptacle, and a valve which is periodically actuated to discharge a dose of feed solution into the vessel.

4. Apparatus according to claim 3, wherein the pump comprises a peristaltic pump.

5. Apparatus according to claim 1, the means to measure dissolved oxygen content comprising a probe, and including means to calibrate the probe.

6. Apparatus according to claim 5, the calibration means comprising means to raise the probe from the liquid, means to add a calibration solution to the probe, and means to expose the probe to substantially 100% humid air in a headspace of the vessel.

7. Apparatus according to claim 6, the means to raise the probe comprising a rack and pinion mechanism operated by a motor.

8. Apparatus according to claim 1, including a means within the vessel whereby to clarify liquid prior to removal from the vessel.

9. Apparatus according to claim 8, the clarifying means comprising an inverted cylinder within the vessel in which the liquid is clarified.

10. Apparatus according to claim 1, comprising an electronic data processing means whereby operation of the apparatus is controlled.

11. A method of monitoring condition of a biomass, comprising the steps of providing a liquid containing a biomass, continuously aerating the liquid containing the biomass, periodically dosing the liquid with feed solution from a dosing means, and measuring dissolved oxygen content of the biomass whereby to monitor the condition of the biomass, the dosing means being continuously fed with the feed solution.

12. A method according to claim 11, the step of measuring the dissolved oxygen content being an electronically controlled measuring step whereby to establish the amount of oxygen utilised per dose of a feed solution.

13. A method according to claim 12, the provision of the liquid comprising providing sewage from a sewage treatment plant.

14. A method according to claim 13, including the steps of providing data relating to sewage flow and combining that flow data with the biomass condition whereby to calculate loadings in a sewage treatment plant.

15. A method according to claim 13, including the steps of monitoring condition of the biomass at an inlet to the plant and at an exit from a primary tank, whereby to provide data relating to oxygen demand of the plant.

16. A method according to claim 11, including the step of determining toxicity of the sewage when a change in the condition of the biomass is detected.

17. Apparatus for monitoring condition of a biomass, comprising a vessel for holding a liquid containing the biomass; a device for continuously aerating the liquid during monitoring of the biomass; means to dose the liquid periodically with feed solution; a pump which continuously feeds the dosing means with the feed solution during monitoring of the biomass; and means to measure the dissolved oxygen content of the liquid to monitor the condition of the biomass, comprising a probe, and means to calibrate the probe comprising means to raise the probe from the liquid, means to add a calibration solution to the probe, and means to expose the probe to substantially 100% humid air in a headspace of the vessel.

* * * * *